United States Patent [19]

Markle

[11] Patent Number: 4,629,796
[45] Date of Patent: Dec. 16, 1986

[54] N-[[2-(1,3-DIHYDRO-1,3-DIOXO-2H-ISOIN-DOL-Z-YL)ETHOXY]METHYL]-Z-PROPENAMIDE

[75] Inventor: Richard A. Markle, Columbus, Ohio

[73] Assignee: Eagle-Picher Industries, Inc., Cincinnati, Ohio

[21] Appl. No.: 738,740

[22] Filed: May 29, 1985

Related U.S. Application Data

[62] Division of Ser. No. 459,778, Jan. 21, 1983, Pat. No. 4,536,582.

[51] Int. Cl.$^4$ ............................................. C07D 209/48
[52] U.S. Cl. ..................................................... 548/477
[58] Field of Search ........................................ 548/477

[56] References Cited

U.S. PATENT DOCUMENTS

| | | | |
|---|---|---|---|
| 2,925,399 | 2/1960 | Schneider et al. | 525/206 X |
| 2,978,432 | 4/1961 | Graulich et al. | 525/142 |
| 2,978,437 | 4/1961 | Christenson | 525/163 |
| 3,037,963 | 6/1962 | Christenson | 525/154 |
| 3,079,434 | 2/1963 | Christenson et al. | 564/208 |
| 3,087,965 | 4/1963 | Dowbenko et al. | 564/208 |
| 3,108,088 | 10/1963 | Krueger | 525/108 |
| 3,118,852 | 1/1964 | Christenson et al. | 525/110 |
| 3,206,424 | 9/1965 | Heimrich et al. | 525/263 |
| 3,240,740 | 3/1966 | Knapp et al. | 526/260 |
| 3,326,868 | 6/1967 | Tucker | 526/304 |
| 3,503,918 | 3/1970 | LeSota et al. | 428/379 |
| 4,059,556 | 11/1977 | Neukam et al. | 526/222 X |
| 4,102,844 | 7/1978 | Schwinum et al. | 524/745 |
| 4,145,500 | 3/1979 | Neukam et al. | 526/204 |
| 4,338,425 | 7/1982 | Dougherty et al. | 524/272 X |
| 4,366,291 | 12/1982 | Gunesin et al. | 526/304 X |

OTHER PUBLICATIONS

Heins, et al., Chem. Abstracts, vol. 98 (1983), Entry 73622.

*Primary Examiner*—Donald G. Daus
*Assistant Examiner*—William A. Teoli, Jr.
*Attorney, Agent, or Firm*—Wood, Herron & Evans

[57] ABSTRACT

A heat curable, solventless liquid prepolymer is prepared from a rubber monomer; a nitrile monomer such as acrylonitrile or methacrylonitrile; and a novel monomer having the following formula:

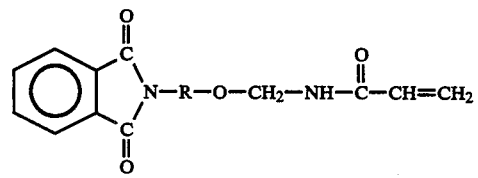

The prepolymer is formed with sufficient chain transfer agent to establish a weight average molecular weight less than about 25,000. This low viscosity prepolymer is heat curable to form a solid rubber polymer suitable for use as a gasket.

1 Claim, No Drawings

N-[[2-(1,3-DIHYDRO-1,3-DIOXO-2H-ISOINDOL-Z-YL)ETHOXY]METHYL]-Z-PROPENAMIDE

This is a division of application Ser. No. 459,778, filed Jan. 21, 1983, now U.S. Pat. No. 4,536,582.

The fabrication of articles from rubber polymers such as isoprene-acrylonitrile copolymers has, in the past, generally involved the evaporation of a solvent. Acrylonitrile rubbers are typically prepared as a solution wherein the polymer is dissolved in an organic solvent. The solvent evaporates, allowing the polymer to dry. The dried rubber polymers are generally so viscous they cannot be applied to a substrate or shaped.

The use of solvent, in this manner, presents two basic problems: cost and health hazards. The solvents themselves are expensive. Although they only act as carriers to facilitate use of the polymer, they are major cost factors. In addition the solvent vapors, formed as the solvent evaporates, are pollutants and general health hazards. These vapors must be trapped or eliminated which is also quite expensive.

One way to overcome the need for a solvent, and to provide a curable polymer, is to form a low molecular weight polymer, commonly referred to as a prepolymer, which is liquid at room temperature and which can be cured to form a satisfactory polymer. Prior art prepolymers have attempted to accomplish this by forming liquid prepolymers having unreacted crosslinkable or reactive terminal groups. Such polymers are known in the art. However, they have certain inherent disadvantages. Primarily, these polymers, in order to cure well and provide good compression set, must have a substantial portion of the end groups made up of the reactive group. For practical reasons, it is difficult to provide a sufficient number of reactive terminal groups so as to provide a liquid polymer which cures to provide a polymer with suitable compression set.

SUMMARY OF THE INVENTION

The present invention comprises a novel self-curing rubber prepolymer having low compression set, i.e., about 20–30%, Shore A hardness of about 70–74%, tensile strength of about 410–640 psi, tensile elongation of about 140%, and fuel resistance of about 49–62%. Polymers having these characteristics are considered to be suitable for various applications including, for example, in gaskets. In a preferred form of the invention, the prepolymer can be used to form strong, smooth rubber sheets suitable for use as commercial gaskets and as laminates also useful as gaskets. Furthermore, novel monomers for use in combination with this prepolymer and prepolymer formed from these monomers are disclosed.

A liquid, heat curable, nitrile rubber is formed from a rubber (i.e., rubber forming) monomer such as isoprene, butadiene or alkyl esters of acrylic acid; a nitrile monomer such as acrylonitrile or methacrylonitrile; and an N-(R-oxymethyl) acrylamide monomer. The latter monomers have the following general formula:

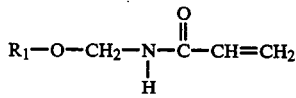

$R_1$ can be $C_3$ to $C_{22}$ alkyl, ether, aldehyde, ketone, amide, ester, imide or a phthalimide. N-(R-oxymethyl) acrylamides where R represents $C_3$–$C_8$ alkyl are readily available.

$R_1$ is preferably a substituent such that the compound $R_1$—OH has a boiling point greater than the cure temperature of the corresponding prepolymer. As will be explained, during the cure of the rubber, the $R_1$ group separates from the prepolymer to form the corresponding alcohol. If the boiling point of the $R_1$ alcohol is less than the cure temperature of the prepolymer, the alcohol will boil, possibly causing a pitting of the surface of the polymer which in certain applications would be unacceptable, such as in the formation of the gasket material.

Preferably, $R_1$ will be a moiety in which the formed alcohol has a boiling point greater than cure temperature of the polymer in which it is employed preferably greater than about 350° F. In addition, the $R_1$ group should be polar in order to make the formed polymer more fuel resistant. $R_1$ must not be a group which will interfere with the chain transfer agent. $R_1$ groups which are non-interfering include ketones, esters and ethers, among others. Interfering groups include those with reactive hydrogens such as alcohols and amines.

Specifically, $R_1$ can represent hexyl carbitol, so that the formed acrylamide monomer would have the following formula:

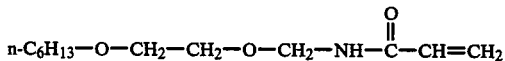

Where $R_1$ is a phthalimide, it is preferably an N-alkyl phthalimide so that the N-(R-oxymethyl) acrylamide has the following general formula:

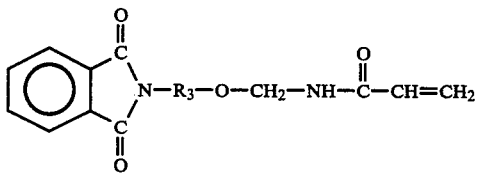

wherein $R_3$ is as $C_1$ to about $C_{10}$ alkyl and preferably has at least two carbon atoms.

These N-(R-oxymethyl) acrylamides can be formed by substituting an $R_1$ group of a monohydric alcohol for the $R_2$ group in an N-(R-oxymethyl) acrylamide having the general formula:

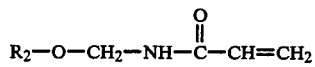

Generally, $R_2$ should be an alkyl group having from 1 to 8 carbon atoms. Such starting materials are commercially available. A description of the method of preparation of these commercially available compounds is disclosed in U.S. Pat. No. 3,087,965, the disclosure of which is incorporated herein by reference. These N-(alkoxymethyl) acrylamides are modified by substituting the alkyl group. For example, a second alcohol, such as hexyl carbitol or 2-hydroxyethyl phthalimide, can be reacted with the N-(alkoxymethyl) acrylamide under acid conditions and elevated temperatures to form the compound of the present invention.

When N-(isobutoxymethyl) acrylamide is used, theoretically equimolar amounts of that compound and a replacement primary alcohol are reacted in the presence of an acid catalyst such as toluene sulfonic acid (for example, 0.5 weight percent based on the acrylamide monomer), at as low a temperature as possible. The isobutyl alcohol formed is vacuum distilled from the reaction mixture until the reaction has gone to completion. In a successful reaction, near theoretical amounts of isobutyl alcohol should be obtained. Excess replacement alcohol may be required to react all of the amide present. This method is further described by reference to the following two examples.

EXAMPLE I

Preparation of N-(hexylcarbitoxymethyl) acrylamide

Predried hexyl carbitol and isobutoxymethacrylamide (IBMA), containing 200 ppm MeHQ, were mixed. An excess of hexyl carbitol (2.9 mole per mole of IBMA) was used. The temperature of the mixture was maintained at less than about 65° C. One half weight percent of toluene sulfonic acid based on the weight of IBMA used was added. Two hundred parts per million of polymerization inhibitor, MEHQ, was added to supplement the 200 parts per million already present in the IBMA. The formed isobutyl alcohol was removed by vacuum distillation. 40.8 weight percent of N-(hexylcarbitoxymethyl) acrylamide in excess hexyl carbitol as solvent was formed. The excess hexyl carbitol was not removed due to its high boiling point.

The disadvantage of using N-(hexylcarbitoxymethyl) acrylamide is that in the preparation, excess hexyl carbitol is required to shift the equilibrium towards the formation of the N-(hexylcarbitoxymethyl) acrylamide. This requires a second step to remove the excess hexyl carbitol or the use of N-(hexylcarbitoxymethyl) acrylamide containing excess hexyl carbitol. Although the excess hexyl carbitol does not prevent the formation of the polymer or the curing of the prepolymer, it apparently does interfere to a certain extent with the polymerization and cure, and the formed product is not as good as would be expected.

EXAMPLE II

Preparation of N-[(2-phthalimidoethoxy)methyl]acrylamide

Approximately equimolar amounts of N-(2-hydroxyethyl phthalimide (about 5 molar percent excess) and dried IBMA were mixed together in a reaction flask with 0.5 weight percent toluene sulfonic acid, based on the weight of IBMA, and 200 ppm MEHQ added. The nearly dry blend was stirred and heated using an external oil bath. When the temperature reached 65° C., a rapid reaction ensued and the reaction mixture partially liquified. After a short period of time, the reaction rate (as evidenced by the isobutyl alcohol removal) almost stopped, and the reaction mixture solidified. The reaction mixture was then rapidly heated to about 120° C., and the reaction again proceeded vigorously, going to near quantitative yields in a few more minutes. The product was a clear, low viscosity liquid at 120° C. which solidified at about 65° C. to a waxy, opaque white solid which was found to be readily soluble in acrylonitrile. The product was the 2-hydroxyethyl phthalimide ether of N-(hydroxymethyl) acrylamide.

Other N-[R-oxymethyl] acrylamides can be made by the transetherification of an alkyloxymethyl acrylamide. An advantage of the use of the 2-hydroxyethyl phthalimide, as opposed to other alcohols, is that there is no need to add excess hydroxyethyl phthalimide to shift the equilibrium over towards the formation of the substituted amide. This is a significant factor where the alcohol is a high boiling point alcohol which is difficult to separate from the formed monomer.

The prepolymer of the present invention also contains an elasticizing or rubber monomer. These rubber monomers include conjugated diolefins, such as isoprene or butadiene and certain esters of acrylic and methacrylic acid. Specifically, any alkyl ester of acrylic acid having two to ten carbons in the alkyl group, and any alkyl ester of methacrylic acid with four to eight carbons in the alkyl group can be used.

Prepolymer Formation

Prepolymers are prepared by mixing from about 65% to about 75% rubber monomer, from about 20% to about 30% acrylonitrile or methacrylonitrile, and from about 4% to about 10% N (R-oxymethyl) acrylamide. In addition, the polymer should have various other components which are well known to those of ordinary skill in the polymer art. These would include a chain transfer agent, such as t-octyl mercaptan. Other such chain transfer agents include $C_6$-$C_{22}$ tertiary mercaptans.

The prepolymerization occurs in an aqueous emulsion. Suitable emulsifiers include fatty acid soaps and anionic sodium dodecylsulphate and commercially available emulsifiers, such as EMCOL 4910, the sodium salt of an unsymmetrical sulfo succinate produced by Witco Chemical.

Chelators, such as disodium ethylene diamine tetra acetic acid are also helpful to remove any interfering metal impurities. Other components to initiate reaction or to increase the speed of the reaction would include a redox activator such as ferric chloride hexahydrate, a reducing agent such as sodium formaldehyde sulfoxylate and a free radical initiator. Suitable free radical initiators would include organic peroxides such as tert-butyl hydroperoxide, di-tertbutyl peroxide, cumene hydroperoxide, dicumene peroxide, benzoyl peroxide and the like. Organic peroxygen compounds such as tertbutyl peracetate, tertbutyl perbenzoate, di-tertbutyl perpthalate are also suitable.

To prepare the prepolymer, the rubber monomer, the acrylonitrile or methacrylonitrile, and the N-(R-oxymethyl) acrylamide can be mixed in the desired proportions within the limits set forth above, together with sufficient chain transfer agent, emulsifier, chelator, activator, reducing agent, free radical initiator and deionized, air-free water. The reactants are mixed and allowed to react for 20-24 hours at about 20° C. by which time yields of about 60-85% are obtained.

The temperature of the reaction should be maintained at less than 40° C., preferably about 20° C. In addition to maintaining the temperature of the reaction within the above limitations, a sufficient amount of a regulator or chain transfer agent must be added to establish the molecular weight of the prepolymer low enough to maintain the desired viscosity. Suitable transfer agents or regulators include n-butyl mercaptan, n-dodecyl mercaptan, t butyl mercaptan, ethyl thioglycolate, as well as t-octyl mercaptan, the preferred chain transfer agent.

The weight average molecular weight of the prepolymer should be established between 5,000 and 25,000, and preferably, between 10,000 and 20,000. The amount of chain transfer agent required will vary depending on the precise monomer used, however, this will generally be less than about 5 weight percent based on the total weight of the monomers. The viscosity of the formed prepolymer desirably should be less than about 50,000 cps at an application temperature of 125° C., or between 90,000 and 150,000 cps at room temperature. Polymers having the above formulation can be fully cured to form a non-flowable solid.

EXAMPLE 3

Isoprene, Acrylonitrile, Isobutoxymethacrylamide Prepolymer (IBMA Prepolymer)

A prepolymer was formed using the following materials:

| Material | Parts by Weight |
|---|---|
| Isoprene | 73 |
| Acrylonitrile | 23 |
| IBMA | 4 |
| t-octyl thiol | 3.5 |
| EMCOL 4910 | 7.5 |
| diNa EDTA | 0.015 |
| FeCl$_3$.6H$_2$O | 0.0075 |
| Na formaldehyde sulfoxylate | 0.2 |
| Diisopropylbenzene hydroperoxide (DIBHP, 50%) | 0.6 |
| H$_2$O (dionized, deaerated) | 210. | pH adjusted to 9.0 with NaOH.

The prepolymerization used a total of 200 grams of monomers, and was run in a large, sealed glass bottle. The above materials were weighed into the bottle. The bottle was purged with argon and sealed. The prepolymerization was run by rotating the bottle on a thermostatically controlled polymerization apparatus using water as a heat transfer medium. The prepolymerization was conducted for 24 hours at 20° C. The prepolymer was recovered by chilling the bottle to about 5° C., opening, adding several hundred milliliters of methanol and stirring vigorously. The aqueous alcohol layer was decanted and the liquid polymer washed with water, dissolved in methylene chloride, rewashed with water and then ethanol, and vacuum dried at 60° C. overnight. Obtained were 110 grams (55%) prepolymer, hereinafter referred to as IBMA prepolymer.

EXAMPLE 4

Isoprene, Acrylonitrile, N-(hexylcarbitoxymethyl) acrylamide Prepolymer (HCMA Prepolymer)

The following components were reacted according to the method described in Example 3;

| Material | Parts by Weight |
|---|---|
| Isoprene | 73 |
| Acrylonitrile | 23 |
| HCMA | 6.8 |
| t-octyl thiol | 3.5 |
| EMCOL 4910 | 7.5 |
| DiNa EDTA | 0.015 |
| FeCL$_3$.6H$_2$O | 0.0075 |
| Na formaldehyde sulfoxylate | 0.2 |
| Diisopropylbenzene hydroperoxide (DIBHP, 50%) | 0.6 |
| H$_2$O (dionized, deaerated) | 210.0 | pH adjusted to 9.0 with NaOH.

70 grams (35%) of N-(hexylcarbitoxymethyl) acrylamide prepolymer were formed, hereinafter referred to as HCMA prepolymer.

EXAMPLE 5

Isoprene, Acrylonitrile, N-[(2-phthalimido ethoxy) methyl] Acrylamide Prepolymer (HPMA Prepolymer)

The following components were reacted according to the method described in Example 3:

| Material | Parts by Weight |
|---|---|
| Isoprene | 73 |
| Acrylonitrile | 23 |
| HPMA | 6.9 |
| t-octyl mercaptan | 3.5 |
| EMCOL 4910 | 7.5 |
| diNa EDTA | 0.015 |
| FeCl$_3$.6H$_2$O | 0.0075 |
| Na formaldehyde sulfoxylate | 0.2 |
| Diisopropylbenzene hydroperoxide (DIBHP, 50%) | 0.6 |
| H$_2$O (deionized, deaerated) | 210.0 | pH adjusted to 9.0 with NaOH.

160 grams (80%) of the N-[(2-phthalimidoethoxy) methyl] acrylamide prepolymer, (hereinafter HPMA prepolymer) were obtained.

Characterization of The Formed Prepolymers

The molecular weight of the formed prepolymers is given below in Table 1.

TABLE 1

PREPOLYMER MOLECULAR WEIGHTS[a]

| Composition | GPC Molecular Weights | | |
|---|---|---|---|
| | Mw | Mn | Mw/Mn |
| IBMA Prepolymer | 14,400 | 5,000 | 2.9 |
| HCMA Prepolymer | 8,700 | 4,800 | 1.8 |
| HPMA Prepolymer | 13,800 | 5,800 | 2.4 |

[a]Gel Permeation Chromatography (GPC), Waters 500, THF solvent at 25° C.; 500, 10$^3$, 10$^4$ A* columns, 7 polystyrene standards —790 to 50,000 M$_w$ All the prepolymers were extremely viscous liquids. However, they were flowable at room temperature and at elevated temperatures such as about 100° C., the viscosity was substantially reduced.

Cure of The Prepolymers

The prepolymers can be further cured to form solid polymers having excellent compression sets, hardness and other physical characteristics required for use as gaskets, coatings and similar applications. Further, the prepolymers can be combined with other materials, such as carbon black, pigments, antioxidants, etc.

The prepolymers are cured by an acid catalyzed method conducted under heat. In order to cure the polymer of the present invention, about 5 weight percent of an acid catalyst, based on the weight of the polymer, is added. Suitable acid catalysts include alkyl or aryl sulfonic acids, mono-alkyl phosphates such a monobutyl phosphate, and trichloro- and trifluoroacetic acids. The catalyst and other components, such as carbon black, are mixed by means such as a rubber mill at room temperature. The mixed composition is then molded and cured by heating to about 360° F., and optionally placed under elevated pressure, until the formed rubber is completely cured.

EXAMPLE 6

Cure of The Prepolymer

The prepolymers formed in the Examples 3, 4 and 5, were each formulated in a 3:2 ratio of prepolymer to carbon black. Five weight percent of p-toluene sulfonic acid was added. The mixture was further compounded in a two roll rubber mill at room temperature for approximately 15 minutes. Each compounded material was molded under heat (360° F.) for 20 minutes in a 6" by 6" by 0.075" mold. Each cured slab was evaluated for the following properties: compression set (70° C. for 22 hours), hardness, tensile strength, elongation and fuel resistance. The results are presented in Table 2, Summary of Physical Property Characterization.

It should be noted that the cured IBMA polymer had a pitted surface.

TABLE 2

| | SUMMARY OF PHYSICAL PROPERTY CHARACTERIZATION | | | | | |
|---|---|---|---|---|---|---|
| t Polymer | Hardness Shore A | Tensile Strength psi | Percent Elongation | Fuel C Resistance[1] % Volume Change | Compression[2] Set | Compressed Original t |
| Prepolymer from Ex. 3 | 89 | 780 | 120 | +45.9 | 30.1 31.5 | 0.720 0.716 |
| Prepolymer from Ex. 4 | 70 | 410 | 140 | +48.8 | 46.0 46.6 | 0.714 0.717 |
| Prepolymer from Ex. 5 | 74 | 640 | 140 | +62.2 | 29.9 32.0 | 0.705 0.710 |

[1]Volume change determined after 24 hour submersion in Fuel C; no solubility or extraction observed.
[2]Conducted at 70° C. for 22 hours.

Gasket Preparation

The polymers of the present invention can be used, for example, to form gaskets. Gaskets are formed by coating both sides of a substrate or base of metal, paper or synthetic material such as cloth, nylon, polyethylene terephthalate, or other suitable materials, with the desired prepolymer formulation. The applied prepolymer is then cured in situ on the base according to the method set forth in Example 6.

The prepolymer and method of formulating the prepolymer of the present invention enables one to prepare a heat-curable polymeric material, which is liquid at application temperatures of 125° C. and less. Furthermore, these prepolymers are curable to form a form polymers which exhibit compression sets which are comparable to other rubber materials suitable for gaskets. This thereby avoids any need for use of a solvent carrier although in certain applications it may be desirable to add a small amount of solvent or a solvent which reacts to form part of the polymer.

Having thus described and claimed my invention, I claim:

1. A monomer having the following general formula:

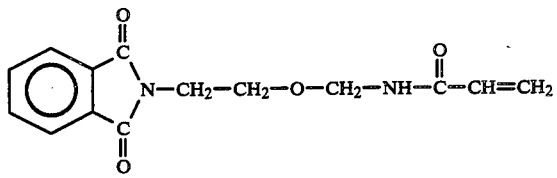

* * * * *

UNITED STATES PATENT AND TRADEMARK OFFICE
CERTIFICATE OF CORRECTION

PATENT NO. : 4,629,796

DATED : December 16, 1986

INVENTOR(S) : Richard A. Markle

It is certified that error appears in the above-identified patent and that said Letters Patent is hereby corrected as shown below:

Please correct the title to read from N-[[1,3-DIHYDRO-1.3-DIOXO-2H-ISOIN-DOL-Z-YL)ETHOXY]METHYL]-Z-PROPENAMIDE to read to N-[[2-(1,3-DIHYDRO-1,3-DIOXO-2H-ISOIN-DOL-2-YL)ETHOXY]METHYL]-2-PROPENAMIDE.

In column 4, line 61, "tbutyl" should be --t-bytul--.

Signed and Sealed this

Twenty-eighth Day of April, 1987

Attest:

DONALD J. QUIGG

*Attesting Officer*    *Commissioner of Patents and Trademarks*